United States Patent
Al-Kofahi et al.

(10) Patent No.: US 11,786,199 B1
(45) Date of Patent: Oct. 17, 2023

(54) X-RAY PENCIL BEAM FORMING SYSTEM AND METHOD

(71) Applicant: Seethru AI Inc., Chelmsford, MA (US)

(72) Inventors: Omar Al-Kofahi, Chelmsford, MA (US); Domenic Anthony Martignetti, Nashua, NH (US)

(73) Assignee: SEETHRU AI INC., Chelmsford, MA (US)

( * ) Notice: Subject to any disclaimer, the term of this patent is extended or adjusted under 35 U.S.C. 154(b) by 0 days.

(21) Appl. No.: 18/123,482

(22) Filed: Mar. 20, 2023

Related U.S. Application Data

(60) Provisional application No. 63/322,696, filed on Mar. 23, 2022.

(51) Int. Cl.
  *A61B 6/00* (2006.01)
  *A61B 6/10* (2006.01)

(52) U.S. Cl.
  CPC ............... *A61B 6/48* (2013.01); *A61B 6/42* (2013.01); *A61B 6/4488* (2013.01); *A61B 6/107* (2013.01); *A61B 6/4071* (2013.01)

(58) Field of Classification Search
  CPC ............................. H05G 1/025; A61B 6/4071
  See application file for complete search history.

(56) References Cited

U.S. PATENT DOCUMENTS

| | | | | | |
|---|---|---|---|---|---|
| 5,056,126 | A * | 10/1991 | Klostermann | ......... | H05G 1/025 378/127 |
| 5,682,412 | A * | 10/1997 | Skillicorn | ............... | H05G 1/10 378/113 |
| 6,075,839 | A * | 6/2000 | Treseder | ............... | H01J 35/064 378/140 |
| 6,252,937 | B1 * | 6/2001 | Snyder | .................. | H01J 35/066 313/30 |
| 6,327,340 | B1 * | 12/2001 | Runnoe | ................ | H01J 35/107 378/132 |
| 6,385,292 | B1 * | 5/2002 | Dunham | ............... | A61B 6/032 378/9 |
| 2005/0175150 | A1 * | 8/2005 | Smith | ...................... | H05G 1/02 378/119 |
| 2005/0201523 | A1 * | 9/2005 | Daniel | ................... | H05G 1/025 378/200 |
| 2007/0098144 | A1 * | 5/2007 | Zhang | ................... | F04D 29/541 378/200 |
| 2007/0140420 | A1 * | 6/2007 | Radley | .................... | H01J 35/12 378/45 |
| 2007/0230663 | A1 * | 10/2007 | Anno | ...................... | H01J 35/13 378/132 |

(Continued)

*Primary Examiner* — Dani Fox
*Assistant Examiner* — Soorena Kefayati
(74) *Attorney, Agent, or Firm* — Witters & Associates; Steve Witters

(57) ABSTRACT

The present disclosure provides systems and methods for create a scanning pencil beam of x-rays and the air cooling of the system. The system has an enclosure with an x-ray beam source disposed therein. An x-ray wheel having or holding an x-ray attenuating ring is disposed proximate to an end of the enclosure and is configured and disposed to rotate the x-ray attenuating ring and form a scanning pencil beam. The system has at least one air inlet and air outlet and at least one air moving device configured and disposed to move air through the air inlet and the air outlet and to air cool the x-ray system.

20 Claims, 9 Drawing Sheets

(56) References Cited

U.S. PATENT DOCUMENTS

| | | | | |
|---|---|---|---|---|
| 2009/0140177 | A1* | 6/2009 | Whittum | H05G 1/10 |
| | | | | 250/493.1 |
| 2012/0002789 | A1* | 1/2012 | Lemarchand | H01J 35/025 |
| | | | | 336/55 |
| 2012/0106714 | A1* | 5/2012 | Grodzins | G01N 23/046 |
| | | | | 378/146 |
| 2015/0124936 | A1* | 5/2015 | Anno | H01J 35/106 |
| | | | | 378/130 |
| 2015/0243469 | A1* | 8/2015 | Mazor | H05G 1/52 |
| | | | | 378/137 |
| 2015/0320376 | A1* | 11/2015 | Oishi | A61B 6/4488 |
| | | | | 378/199 |
| 2015/0371809 | A1* | 12/2015 | Ding | H05G 1/12 |
| | | | | 378/101 |
| 2017/0167989 | A1* | 6/2017 | Crosby | G01N 23/223 |
| 2017/0171953 | A1* | 6/2017 | Kikuchi | H05G 1/025 |
| 2019/0297717 | A1* | 9/2019 | Kondo | G01N 23/04 |
| 2019/0298286 | A1* | 10/2019 | Kuehn | A61B 6/4488 |
| 2020/0008287 | A1* | 1/2020 | Heuft | H05G 1/025 |
| 2020/0289074 | A1* | 9/2020 | Zilberstien | G01T 1/244 |
| 2020/0315057 | A1* | 10/2020 | Kuehn | A61B 6/035 |
| 2021/0014956 | A1* | 1/2021 | Ishii | H01J 35/00 |
| 2021/0029808 | A1* | 1/2021 | Ishii | H05G 1/025 |
| 2021/0082655 | A1* | 3/2021 | Havla | H01J 35/18 |
| 2021/0407759 | A1* | 12/2021 | Rommel | H01J 35/12 |
| 2022/0087625 | A1* | 3/2022 | Keller | A61B 6/4488 |

\* cited by examiner

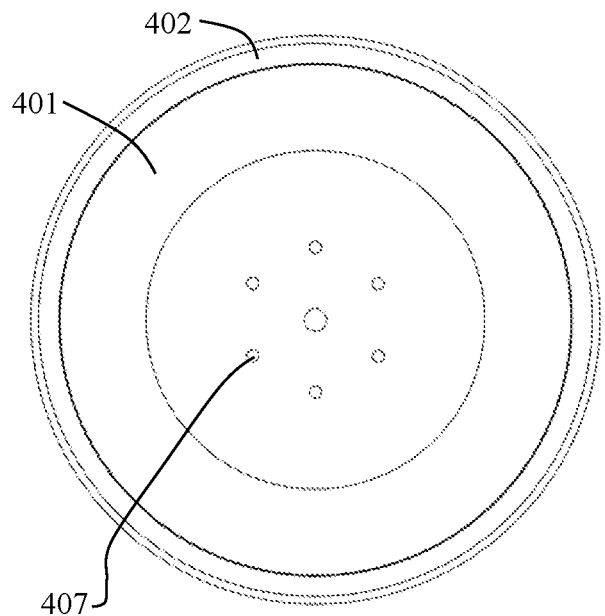
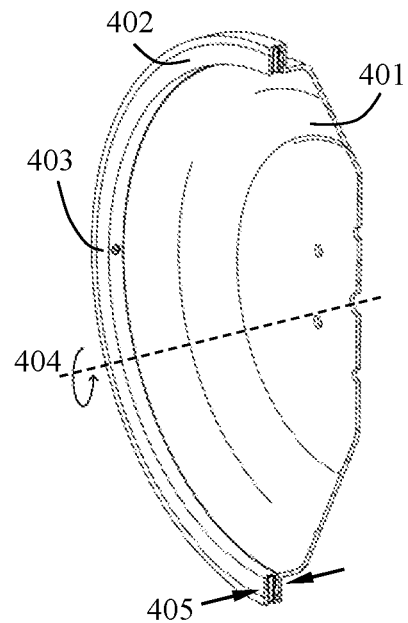
FIG. 4A    FIG. 4B
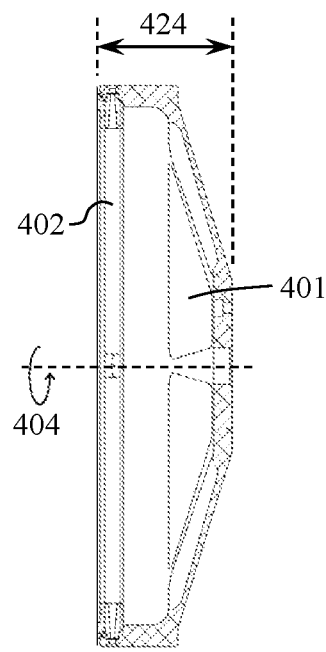
FIG. 4C

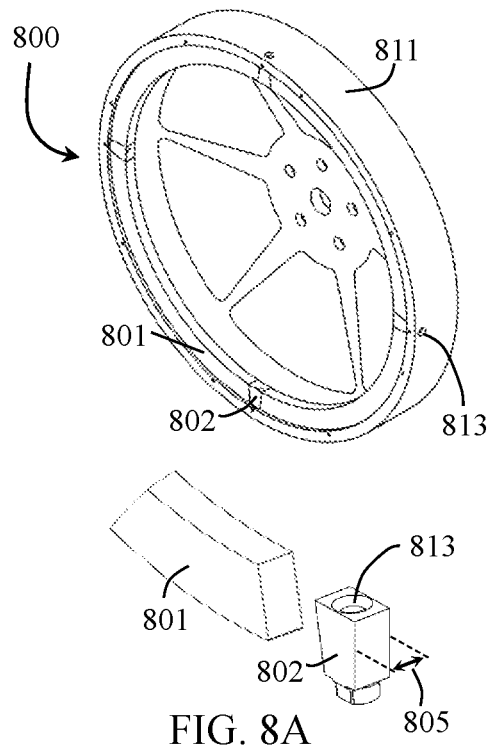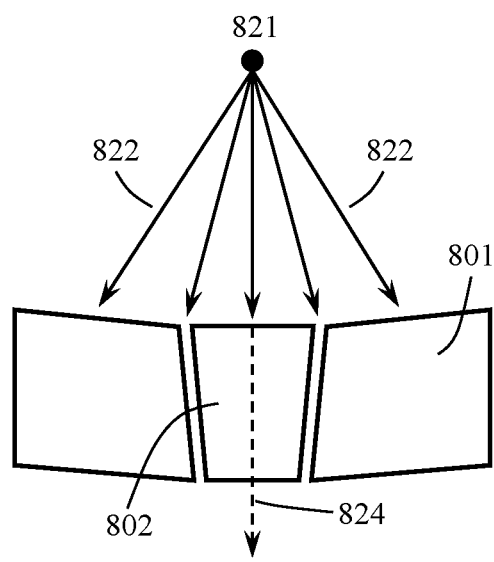
FIG. 8A
FIG. 8B
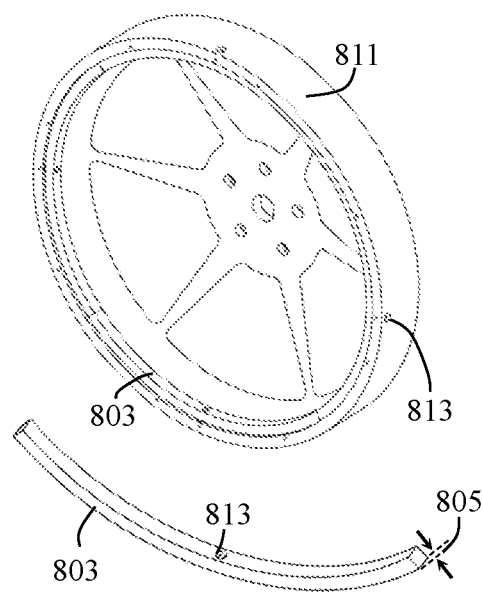
FIG. 8C

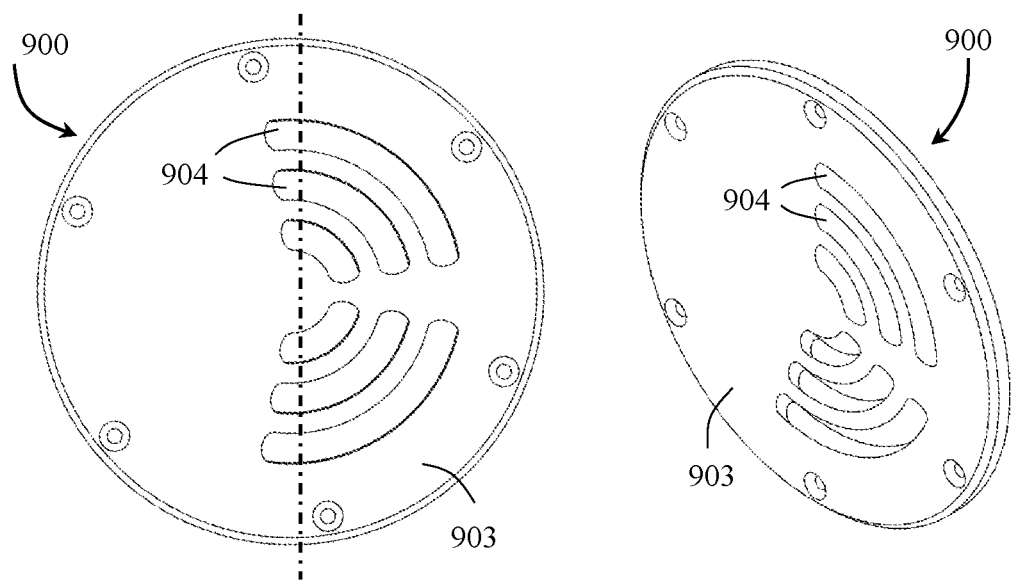
FIG. 9A
FIG. 9B
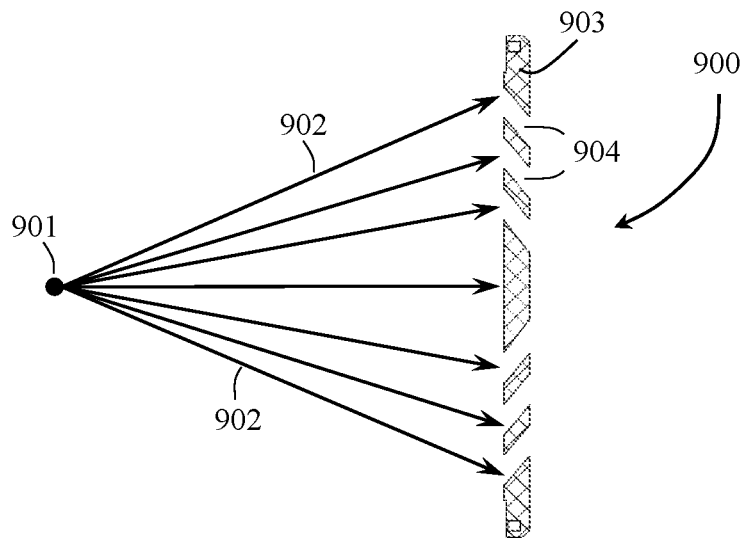
FIG. 9C

X-RAY PENCIL BEAM FORMING SYSTEM AND METHOD

CROSS REFERENCE TO RELATED APPLICATIONS

This application claims priority to U.S. provisional application No. 63/322,696, filed Mar. 23, 2022, the disclosure of which is hereby incorporated by reference in its entirety.

FIELD OF INVENTION

The present disclosure relates to non-intrusive inspection of objects with x-rays such as inspection with an x-ray pencil beam forming systems and methods inspection.

BACKGROUND OF THE INVENTION

X-ray radiation is commonly used to perform non-intrusive inspection (NII) of objects. Examples include industrial, medical and security inspection. To perform imaging, an x-ray beam is typically formed into a cone beam, a fan beam, or a scanning pencil beam. FIG. 1A illustrates an x-ray source 101 emitting an x-ray beam formed in the shape of a cone 102 with a solid angle spanning more than 0.1 steradians and a cross-section that is typically elliptical or rectangular, and a length 103 to width 104 ratio close to 1.0. A fan beam, as illustrated in FIG. 1B, has a substantially planar shape 105 and a length 107 to width 106 ratio substantially greater than 1.0. A scanning pencil beam 108, as illustrated in FIG. 1C, is narrow, spanning a solid angle smaller than 0.02 steradians, and is moved to cover a substantially planar region.

There are two configurations of x-ray tubes disclosed herein, unipolar and bipolar. A unipolar x-ray tube, as the name suggests, takes a single polarity power as input. For example, a unipolar x-ray tube with peak energy of 225 kV takes a single power input with voltage equal to about 225 kV. In contrast, a bipolar x-ray tube takes two power inputs with opposite polarities. For example, a bipolar x-ray tube with peak energy of about 320 kV takes two power inputs: +160 kV and −160 kV such that the end-to-end voltage difference is 320 kV.

In an x-ray tube, only a small fraction of the electrical energy is converted to x-rays and the majority of the energy is converted to heat which must be removed from the x-ray tube to avoid damaging it. There are two common methods for cooling an x-ray tube, liquid and air cooling. In the first method, a liquid, such as water or oil, circulates through the x-ray tube to carry the heat out of the tube. The liquid then goes through a heat exchange mechanism to reduce its temperature before recirculating through the tube. In the second method, air is used instead of the liquid to remove the heat from the x-ray tube. An air cooled x-ray tube typically comprises air-to-air heat exchange surfaces to remove the heat from the tube.

As illustrated in FIG. 2A, a unipolar x-ray tube 210 comprises a body 204 and a receptacle 201, where an electrical power is applied. Part of the input electrical energy is then converted to x-rays which exit the tube through a beam window 202, where the primary x-ray beam exits the x-ray tube. Beam window 202 typically has a rectangular, circular, or elliptical shape. Liquid cooled x-ray tubes further comprise an inlet and outlet 203 for the liquid coolant to circulate through the x-ray tube. A bipolar x-ray tube, as illustrated in FIG. 2B, comprises two receptacles 201 for the bipolar power inputs. Similar to a unipolar x-ray tube, a bipolar tube also comprises a body 204, an x-ray beam window 202 and liquid inlet and outlet 203 for liquid cooled x-ray tubes. The power receptacles and liquid coolant inlet and outlet are commonly positioned on the tube ends as illustrated in FIGS. 2A and 2B, but may alternatively be positioned in other places on the tube body.

In addition to the primary x-ray beam emitted through the beam window 202, some x-rays typically leak through the x-ray tube body 204. When using an x-ray scanning pencil beam for imaging, it is typically important to substantially shield all x-rays except for those within the scanning pencil beam. Hence, the entire body of the x-ray tube is typically placed within a shielded enclosure comprising x-ray attenuating material, including without limitation, lead or tungsten. This shielded enclosure may make it difficult to use air to cool an x-ray tube as the enclosure may limit air circulation. Hence, liquid cooling is often used to cool unipolar x-ray tubes used in scanning pencil beam imaging systems, most notably with x-ray tubes with peak energies greater than 200 kV.

It may be desirous to provide an air cooled x-ray system configured to form a scanning pencil beam of x-rays.

SUMMARY

In one aspect of the present disclosure, an air cooled x-ray system configured to form a scanning pencil beam of x-rays is provided. The x-ray system has an enclosure with a first end and an opposite second end. An x-ray beam source is disposed in the enclosure proximate its first end. An x-ray wheel having or holding an x-ray attenuating ring is disposed proximate to the first end of the enclosure, the x-ray attenuating ring has at least one aperture in an outer circumference thereof. The x-ray wheel is configured and disposed to rotate the x-ray attenuating ring about the x-ray beam source and for the passage of x-rays through the at least one aperture and forming the scanning pencil beam. At least one air inlet and at least one air outlet are disposed in x-ray system. At least one air moving device is configured and disposed to move air through the air inlet and the air outlet and to air cool the x-ray system. The enclosure comprises an x-ray attenuating material and is configured and disposed to substantially limit x-ray leakage from the x-ray system.

In another aspect of the present disclosure, a method of air cooling a scanning pencil beam x-ray system is provided. The method comprises disposing an x-ray beam source proximate a first end of an enclosure; rotating an x-ray attenuating ring about the x-ray beam source; disposing at least one aperture in an outer circumference of the x-ray attenuating ring to x-rays generated with the x-ray beam source and forming a scanning pencil beam of x-rays; moving air into an air inlet in the enclosure; moving the air about the x-ray beam source and absorbing heat generated with the x-ray beam source; and moving the heated air out of the enclosure and thereby air cooling the scanning pencil beam x-ray system.

BRIEF DESCRIPTION OF THE DRAWINGS

The foregoing and other features of this disclosure will become more fully apparent from the following description and appended claims, taken in conjunction with the accompanying drawings and examples. Understanding that these drawings depict only several embodiments in accordance with the disclosure and are therefore not to be considered limiting of its scope. The disclosure will be described with additional specificity and detail through use of the accompanying drawings.

The following figures, which are idealized, are not to scale and are intended to be merely illustrative of aspects of the present disclosure and non-limiting. In the drawings, like elements may be depicted by like reference numerals. The drawings are briefly described as follows:

FIGS. 4A and 4B illustratively show a front view and a sectional view, respectively, of an x-ray wheel having or holding an x-ray attenuating ring that may be incorporated with the presently disclosed system;

FIG. 4C illustratively shows cross-sectional view of an x-ray wheel having or holding an x-ray attenuating ring that may be incorporated with the presently disclosed system;

FIG. 8A illustratively shows an embodiment of an x-ray wheel holding a sectioned x-ray attenuating ring that may be incorporated with the presently disclosed system;

FIG. 8B illustratively shows the forming of a pencil beam with the sectioned x-ray attenuating ring shown in FIG. 8A;

FIG. 8C illustratively shows another embodiment of an x-ray wheel holding an x-ray attenuating ring that may be incorporated with the presently disclosed system; and FIGS. 9A-9C illustratively show views of an enclosure cap that may be incorporated with the presently disclosed system.

DETAILED DESCRIPTION OF THE INVENTION

Presently disclosed is an air cooled x-ray system configured to form a scanning pencil beam of x-rays and method. Liquid cooling is often used to cool unipolar x-ray tubes used in scanning pencil beam imaging systems, most notably with x-ray tubes with peak energies greater than 200 kV. Embodiments of the presently disclosed system have a shielded enclosure configured to enable the use of air-cooled x-ray tubes in scanning pencil beam imaging systems. In at least one embodiment of the present disclosure, the x-ray tube has its window disposed proximate its end. For example, this may enable the presently disclosed shielded enclosure to enclose a substantial portion of a longitudinal perimeter of the x-ray tube and to enable the disposition of its window proximate, or just outside of, an end of the shielded enclosure for attenuation of the x-rays emitted by the source. Currently, unipolar x-ray tubes are configured to have their window disposed proximate an end of their tube. Other and different x-ray sources, such as bipolar x-ray tubes, may become available for a disposition of their window proximate their end. Therefore, the presently disclosed air cooled x-ray system configured to form a scanning pencil beam of x-rays is not limited to unipolar x-ray tubes.

Figure 1A:
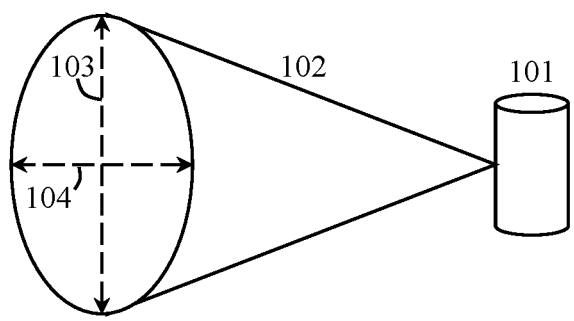
FIG. 1A illustratively shows an x-ray source emitting an x-ray beam formed in the shape of a cone.

As used herein and in any appended claims, the following terms shall be defined as follows:

"Cone beam," shall refer to a beam of x-rays formed into a cone 102 as illustrated in FIG. 1A, typically with a circular, elliptical, or rectangular cross-section, and a length 103 to width 104 ratio close to 1.0. A cone beam spans a solid angle larger than 0.1 steradians.

Figure 1B:
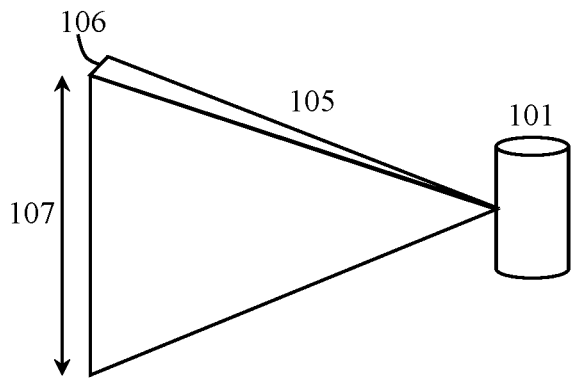
FIG. 1B illustratively shows an x-ray source emitting an x-ray beam formed in a fan shape.

"Fan beam," shall refer to a beam of x-rays that is substantially planar 105 as illustrated in FIG. 1B, and a length 107 to width 106 ratio substantially greater than 1.0.

"Fan beam collimator," shall refer to an apparatus used to form an x-ray fan beam.

Figure 1C:
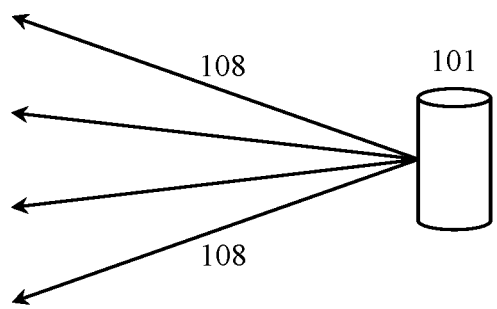
FIG. 1C illustratively shows the emitting of an x-ray scanning pencil beam.

"Scanning pencil beam," shall refer to a narrow beam of x-rays 108 spanning a solid angle of less than 0.02 steradians. The pencil beam is moved in a substantially planar region as illustrated in FIG. 1C.

"Beam plane," shall refer to a substantially planar region subtended by a fan beam or a scanning pencil beam.

"Shielded enclosure," shall refer to an enclosure housing an x-ray tube which substantially limits x-ray leakage emitted from an x-ray tube. The enclosure contains x-ray attenuating material, including without limitation, lead or tungsten.

"Pencil beam bore," shall refer to a hole, aperture, or opening, 322 or 813, within an x-ray attenuating ring 301 or a ring segment 802 or 803.

"Pencil beam aperture," shall refer to a piece of x-ray attenuating material with an aperture 322 allowing x-rays to pass through creating a scanning pencil beam.

Presently disclosed is an x-ray pencil beam forming system which is used in x-ray scanning pencil beam imaging. The system comprises an x-ray tube, a shielded enclosure, a fan beam collimator, an x-ray wheel, and a means or configuration for air cooling the system.

Currently, x-ray imaging systems comprising a scanning pencil beam commonly use unipolar x-ray tubes as they are typically smaller than bipolar tubes. Further, a unipolar tube is typically enclosed inside a shielded enclosure to limit x-ray leakage which can negatively impact the imaging performance. The present disclosure provides embodiments for efficient air cooling of unipolar x-ray tubes with peak energies greater than 200 kV used in x-ray scanning pencil beam imaging systems. It is to be understood the presently disclosed air cooled x-ray system configured to form a scanning pencil beam of x-rays is not limited to unipolar x-ray tubes.

In x-ray scanning pencil beam imaging systems, a fan beam collimator is used to shape the x-ray beam into a fan beam which is then reduced into a scanning pencil beam. The present disclosure provides novel compact fan beam collimator embodiments which fit in tight spaces.

FIGS. 1A-1C Illustrate x-ray beam shapes emitted from an x-ray source 101. FIG. 1A shows a cone beam 102, typically with an elliptical or rectangular cross-section, spanning a solid angle greater than 0.1 steradians, and having a length 103 to width 104 ratio close to 1.0. FIG. 1B shows an x-ray fan beam 105 which is substantially planar with a length 107 to width 106 ratio substantially greater than 1.0. FIG. 1C shows an x-ray scanning pencil beam 108 which is moved in a substantially planar region and spanning a solid angle less than 0.02 steradians.

Figure 2A:
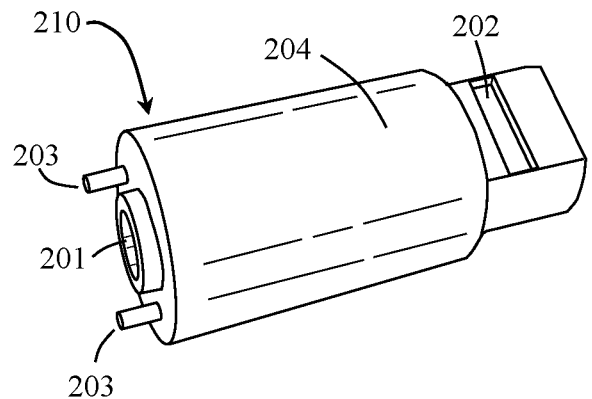
FIG. 2A illustratively shows a unipolar x-ray tube.
Figure 2B:
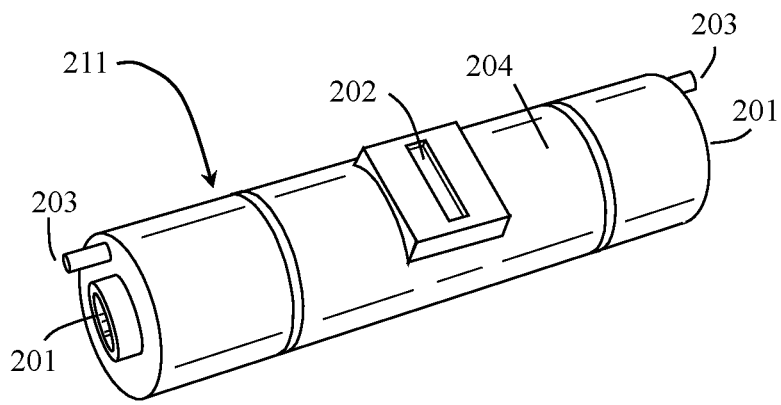
FIG. 2B illustratively shows a bipolar x-ray tube.

There are two x-ray tube configurations commonly used in scanning pencil beam imaging systems, unipolar and bipolar, as illustrated in FIGS. 2A and 2B. When powered, an x-ray tube generates heat and hence requires cooling which is performed by passing a liquid or air through the x-ray tube. These cooling methods are referred to as liquid cooling and air cooling, respectively.

FIG. 2A. illustrates a unipolar x-ray tube comprising a body 204, a power cable receptacle 201, and a beam window 202, where the primary x-ray beam exits the x-ray tube. In liquid cooled x-ray tubes, the tube further comprises and inlet and outlet 203 for the liquid to circulate through the tube. FIG. 2B shows a bipolar x-ray tube comprising a body 204, two power cable receptacles 201, and a beam window 202, where the primary x-ray beam exits the x-ray tube. In liquid cooled x-ray tubes, the tube further comprises and inlet and outlet 203 for the liquid to circulate through the tube.

Unipolar x-ray tubes, as illustrated in FIG. 2A, are commonly used in x-ray imaging applications comprising a scanning pencil beam. In a unipolar x-ray tube, the primary x-ray beam is emitted from a beam window 202 located near the tube end, as opposed to near the tube center in current bipolar tubes (FIG. 2B). In addition to the primary x-ray beam 202, an x-ray tube may also leak x-rays through its body 204. This x-ray radiation leakage negatively impacts the imaging performance and hence an x-ray tube is typically enclosed inside a shielded enclosure limiting the x-ray leakage. The enclosure also restricts air circulation about the x-ray tube making air cooling of the x-ray tube less efficient. The present disclosure provides embodiments for efficient air cooling of x-ray tubes with peak energy greater 200 kV, enclosed in shielded enclosures and used in scanning pencil beam imaging systems. In at least one embodiment of the present disclosure, the x-ray source has its window disposed proximate its end, such as illustrated with the current design of a unipolar x-ray tubes.

Figure 3A:
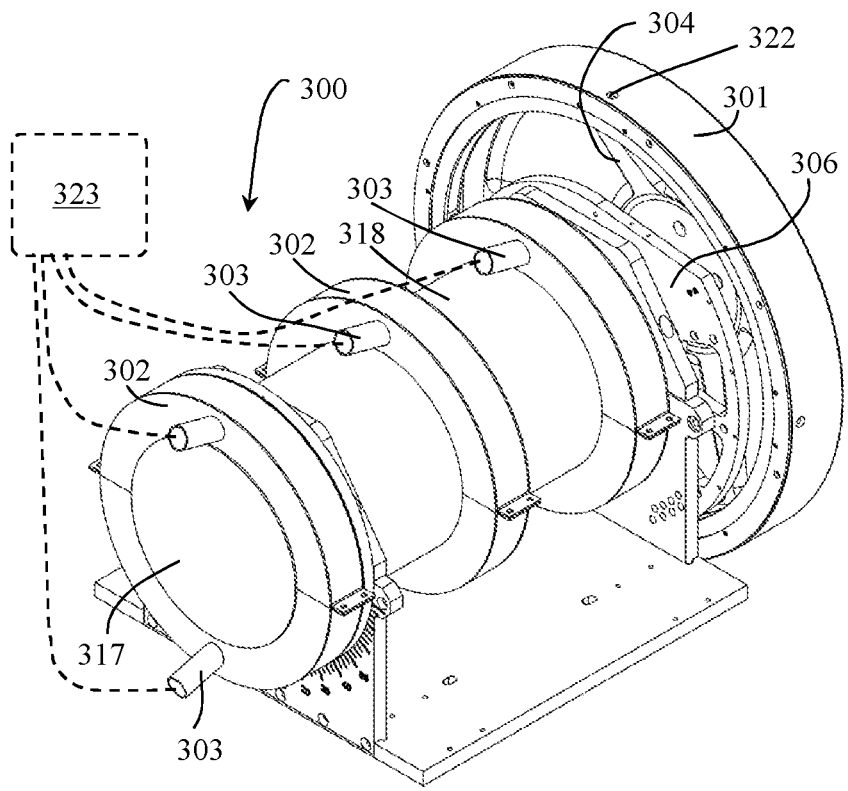
FIG. 3A illustratively shows an air cooled x-ray system configured to form a scanning pencil beam of x-rays of the present disclosure.

FIG. 3A illustratively shows an air cooled x-ray system 300 configured to form a scanning pencil beam of x-rays of the present disclosure. X-ray system 300 has a shielded enclosure 318, a fan beam collimator 306, an x-ray wheel 304 having or holding an x-ray ring, or attenuating ring, 301. Enclosure 318 may have at least one of an air inlet and an air outlet 303 and a plenum or chamber 302 disposed about its outer surface. Plenum or chamber 302 is configured and disposed to direct air flow through the at least one air inlet and outlet in enclosure 318 for air cooling x-ray system 300. For example, an air moving device, schematically and illustratively depicted as 323, such as a fan may be configured and disposed to move air into or out of ports 303.

Attenuating ring 301 may be disposed about a first end 321 of enclosure 311 or 318. One or both ends, 319 and 321, of the enclosure may be open or may have an x-ray shield comprising an x-ray attenuating material disposed to substantially limit x-ray leakage into an ambient environment. For example, an x-ray shield may be disposed remote from the enclosure or may be disposed with an end, 319 and/or 321 of enclosure 318 or 311, such as x-ray shield 317 or enclosure cap 900, shown in FIG. 9A.

Figure 3B:
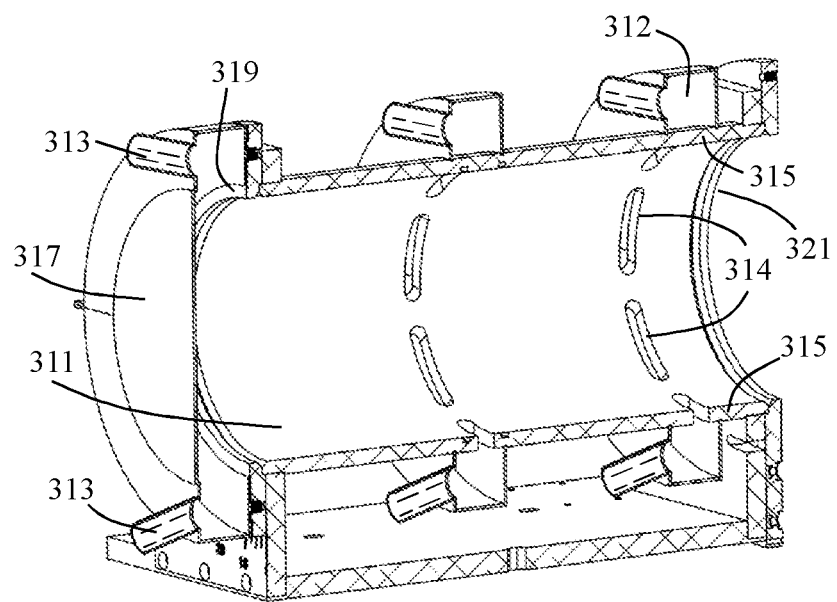
FIG. 3B illustratively shows an enclosure that may be incorporated with the presently disclosed system.

FIG. 3B illustratively shows enclosure 311 that may be incorporated with the presently disclosed air cooled x-ray system configured to form a scanning pencil beam of x-rays. Enclosure 311 has at least one air inlet or air outlet 314 and plenum or chamber 312 disposed about its outer surface. Plenum or chamber 312 is configured and disposed to direct air flow through at least one air inlet and/or outlet 314 in enclosure 311 for air cooling the x-ray system. For example, an air moving device such as a fan may be configured and disposed to move air into or out one or more ports 313. In at least one embodiment, enclosure 311 has a cylindrical sidewall 315 with a first end 321 and an opposite second end 319.

With reference to FIGS. 3A and 3B, an air cooled x-ray system configured to form a scanning pencil beam of x-rays is shown. The x-ray system has an enclosure, for example enclosure 318 or 311, with a first end 321 and an opposite second end 319. An x-ray beam source is disposed in the enclosure proximate its first end. For example, a unipolar x-ray tube may be disposed in the enclosure and may have a window for emitting x-rays proximate first end 321. It is to be understood the presently disclosed air cooled x-ray system configured to form a scanning pencil beam of x-rays is not limited to unipolar x-ray tubes.

An x-ray wheel 304 may have or hold an x-ray attenuating ring 301 proximate to first end 321 of the enclosure. X-ray attenuating ring 301 has at least one aperture or pencil beam bore 322 in an outer circumference thereof. X-ray wheel 304 is configured and disposed to rotate x-ray attenuating ring 301 about the x-ray beam source and for the passage of x-rays through the at least one aperture 322 and forming the scanning pencil beam.

At least one air inlet and at least one air outlet is disposed in the x-ray system. For example, one or more air inlets and air outlets may be disposed in a sidewall of the enclosure, such as air inlet or outlet 314, first end 321, and/or second end 319. At least one air moving device is configured and disposed to move air through the air inlet and the air outlet and to air cool the x-ray system. For example, x-ray wheel 304 may be configured to move air into or out of first end 321. Alternatively or additionally, an air moving device such as a fan may be configured and disposed to move air through the system. In at least one embodiment, the enclosure has at least one of the air inlets and outlets and a plenum or chamber disposed about its outer surface, the plenum or chamber is configured and disposed to direct air flow through the at least one air inlet and outlet 314 in the enclosure for air cooling the x-ray system. In at least one additional embodiment, at least one of the air moving devices is disposed outside of a perimeter of the x-ray wheel 304 and the enclosure.

The enclosure comprises an x-ray attenuating material and is configured and disposed to substantially limit x-ray leakage from the x-ray system. For example, the enclosure may be configured to not exceed 10 micro sieverts at a distance of 1 meter. In at least one embodiment, the x-ray system has at least one x-ray shield having an x-ray attenuating material, the at least one x-ray shield is configured and disposed to substantially limit x-ray leakage into an ambient environment from at least one of first end 321 and second end 319 of the enclosure. For example, the x-ray shield may be configured to not exceed 10 micro sieverts at a distance of 1 meter. The x-ray shield may have an end enclosure cap, such as end enclosure 900 shown in FIG. 9A, disposed with or proximate first end 321, second end 319, or both ends of the enclosure. The enclosure cap may have at least one air inlet or air outlet. In at least one embodiment, the x-ray wheel comprises an x-ray attenuating material configured and disposed to substantially limit x-ray leakage from the x-ray system.

FIGS. 3A and 3B illustrate embodiments of a shielded enclosure for a unipolar x-ray tube, with peak energy greater than 200 kV, used in a scanning pencil beam imaging system. The shielded enclosure comprises an x-ray attenuating material with one or more holes, openings, or apertures, such as air inlets or outlets 314, which allow air to flow into or out of the shielded enclosure. The enclosure may comprise one or more plenums 302 or 312 configured and disposed to distribute air into or out of the shielded enclosure through the one or more openings. Each of the plenums comprises one or more conduits or ports 303 or 313 which allow air to flow into or out of the plenums. The shielded enclosure in at least one embodiment is substantially cylindrical with parallel edges.

In at least one embodiment, a shielded enclosure is configured to hold a unipolar x-ray tube with peak energy greater than 200 kV and provide an imaging system with a scanning pencil beam. The shielded enclosure comprises a main body which longitudinally encompasses the x-ray tube. To attenuate the x-ray leakage from the x-ray tube, the shielded enclosure body may comprise a layer of lead that may be at least 2 mm thick. Alternative embodiments may comprise other materials with thicknesses which achieve an x-ray attenuation equivalent to 2 mm of lead, or more. Alternative embodiments of the shielded enclosure may be configured to hold or enclose a length of an x-ray source other than a unipolar x-ray tube.

The shielded enclosure of at least one embodiment further comprises one or more air flow openings, such as air inlets or outlets 314, which allow air to flow into or out of the shielded enclosure to perform air cooling of the x-ray tube. One or more plenums may be aligned with the one or more air flow openings. The one or more plenums may improve the uniformity of air flow into and out of the shielded enclosure body. Further, the one or more plenums may comprise x-ray attenuating material including without limitation steel, lead, or tungsten, to attenuate x-ray radiation leaking through the one or more air flow openings. The optimal number of plenums and their positions on the shielded enclosure depends on several factors, including the size, shape, energy and power of the x-ray source, and the temperature and pressure of the cooling air. Hence, while the embodiments shown in FIGS. 3A and 3B comprises three plenums, other embodiments may comprise one or two plenums, while others may comprise four or more plenums. Each of the one or more plenums have one or more air inlets or outlets or ports 303 or 312 to allow air to flow into or out of the plenums and through the enclosure.

The plenums used in the embodiments shown in FIGS. 3A and 3B may cover the entire circumference of the shielded enclosure body as illustrated in FIGS. 3A and 3B. Other embodiments may comprise one or more plenums which only partially cover the circumstance of the shielded enclosure. Further embodiments may be configured to circulate air directly through the one or more air flow openings, such as air inlets or outlets 314, and hence may not require any plenum. Yet other embodiments may comprise one or more openings at the first or second ends of the shielded enclosure, along its longitudinal axis, for air to flow in or out of the shielded enclosure. In at least one embodiment, the enclosure may be void of air inlets and outlets 314 and the system may be configured to pass cooling air through enclosure ends 319 and 321.

In at least one embodiment of the present disclosure, the shielded enclosure is cylindrical and surrounds a cylindrical x-ray source, wherein the enclosure and the x-ray source have a common longitudinal axis. For example, the enclosure may be configured to substantially surround the outer sidewall of the x-ray source, such as the unipolar x-ray source shown in FIG. 2A. It is to be understood that the shielded enclosure is not limited to the cylindrical shape, as the enclosure may have other cross-sectional shapes such as elliptical, rectangular, or polygonal, for example. Additionally, the shielded enclosure may not have a consistent cross-sectional shape throughout its longitudinal axis. For example, the enclosure may be conical or have an irregular shape.

FIGS. 4A and 4B illustratively show a front view and a sectional view, respectively, of an x-ray wheel 401 having or holding an x-ray attenuating ring 402 that may be incorporated with the presently disclosed system. In at least one embodiment, an x-ray wheel 401 comprises an attenuating ring 402 which absorbs x-rays and further comprises one or more pencil beam bores or apertures 403 which allow one or more scanning pencil beams to exit. Rotating x-ray wheel 401 around its axis 404 forms one or more scanning pencil beams sweeping a beam plane. To avoid breaking the attenuating ring 402 around the pencil beam bores 403, the ring width 405 must be sufficiently greater than that of the pencil beam bores 403.

In at least one embodiment, x-ray wheel 401 comprises an x-ray attenuating ring 402 made of x-ray attenuating material, including without limitation lead or tungsten, which blocks an x-ray beam plane except for one or more holes or apertures 403, referred to herein as pencil beam bores or apertures 403. The x-ray wheel rotates around a central axis 404 causing scanning pencil beams to sweep over a plane. To maintain structural integrity and avoid breaking the attenuating ring 302 around the pencil beam bores 403, the width 405 of the attenuating ring must be greater than that of the pencil beam bores 403, which in turn increases the overall volume and weight of the ring 402. As the energy of the x-rays increases, so does the weight of the x-ray attenuating ring 402 as more material is required to stop the x-rays. To maintain the structural integrity of the x-ray wheel 401 against the centrifugal force resulting from the rotating x-ray attenuating ring 402, it is common to limit system parameters including the rotational speed of the x-ray wheel, its diameter, the x-ray energy, or a combination of these parameters. The present disclosure provides embodiments to reduce the weight of the x-ray attenuating ring 402 thus relaxing constraints on the system parameters, such as the embodiments shown in FIGS. 8A-8C.

FIGS. 4C and 4D illustratively show cross-sectional views of x-ray wheels 401 having or holding x-ray attenuating rings 402 that may be incorporated with the presently disclosed system. To form an x-ray scanning pencil beam, an x-ray attenuating ring 402, made of x-ray attenuating material, including without limitation lead or tungsten, is mounted on an x-ray wheel 401. The ring comprises one or more x-ray pencil beam bores 403 which allow one or more pencil beams to exit the ring as illustrated in FIGS. 4A and 4B. Rotating the x-ray wheel around its center 404 causes the one or more pencil beams to sweep a beam plane. The weight of the attenuating ring increases as the peak energy of the x-ray tube increases since more attenuating material is needed to absorb the higher x-ray energy. The weight of the ring also increases as its radius increases. The centrifugal force generated as the attenuating ring rotates around an axis 404 ads limiting constraints on system parameters including the rotational speed of the attenuating ring 402 and x-ray wheel 401, its radius, peak x-ray energy, or a combination of the parameters.

In at least one embodiment, the enclosure is configured to substantially surround a longitudinal outer surface of an x-ray source, such as unipolar x-ray source 204. The x-ray source may have its window 202 disposed proximate, or just outside of, first end 321 of the enclosure. X-ray wheel 401 may be configured to be disposed on a rotating mechanism with attachment openings or areas 407. For example, x-ray wheel 401 may be attached to a rotatable spindle with fasteners cooperating with openings 407. X-ray wheel 401 is configured and disposed to rotate attenuating ring 402 about the x-ray beam source such as window 202. For example, attenuating ring 402 may be disposed substantially radially with window 202. It may be advantageous for x-ray wheel 401 to have a minimum depth 424. For example, a minimized depth 424 may provide structural advantages for x-ray wheel 401 to hold and spin attenuating ring 402 as the centrifugal force places stress on x-ray wheel 401. In at least one embodiment of the present disclosure, x-ray wheel 401 has a depth 424 not to exceed 6 inches. Such a depth may be achieved by disposing an air moving device with x-ray wheel 401 or by disposing the air moving device outside of a perimeter of the x-ray wheel and the enclosure. In at least one embodiment of the present disclosure, the system is void of an air moving device disposed between the enclosure and x-ray wheel 401.

Figure 5A:
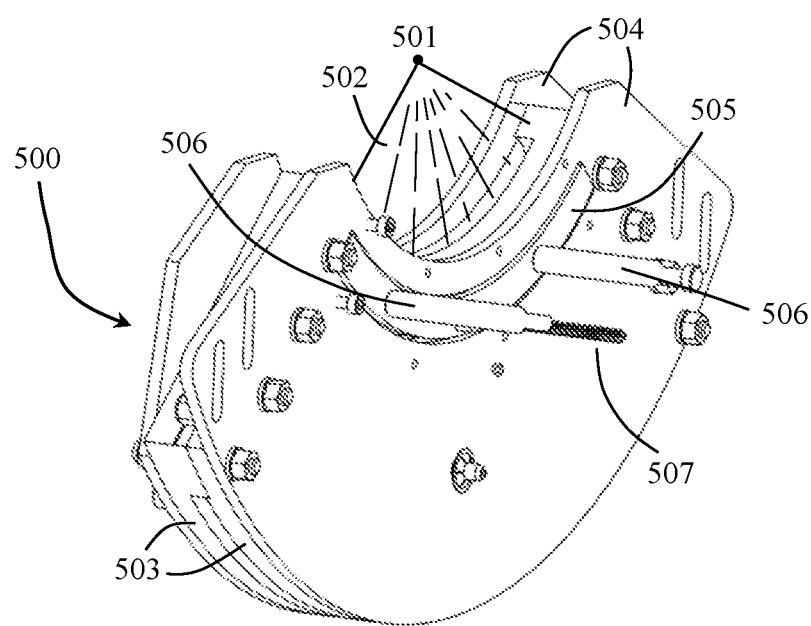
FIG. 5A illustratively shows a collimator that may be incorporated with the presently disclosed system.
Figure 5B:
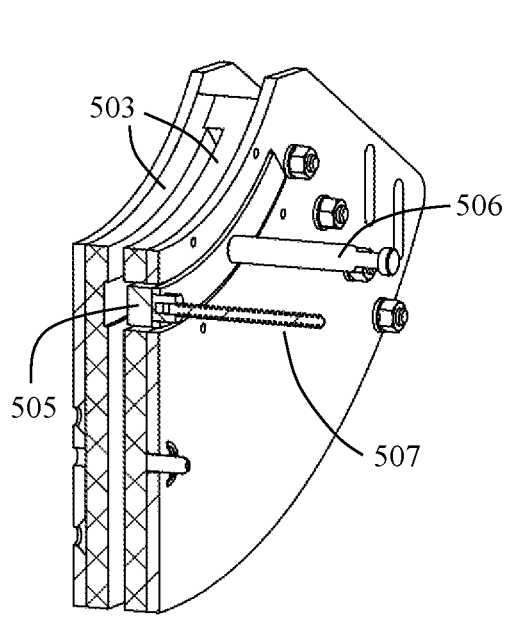
FIG. 5B is a sectional view of the fan beam collimator shown in FIG. 5A, illustratively showing a shutter in an open position.

FIG. 5A illustratively shows a collimator 500 that may be incorporated with the presently disclosed x-ray pencil beam forming system. FIG. 5B is a sectional view of fan beam collimator 500 illustratively showing a shutter in an open position and FIG. 5C shows fan beam collimator having 500 having the shutter in a closed position.

In x-ray scanning pencil beam imaging systems, fan beam collimator 500 may be used to shape the x-ray beam into a fan beam which is then reduced into a scanning pencil beam. Fan beam collimator 500 may be compact fit in tight spaces.

Figure 5C:
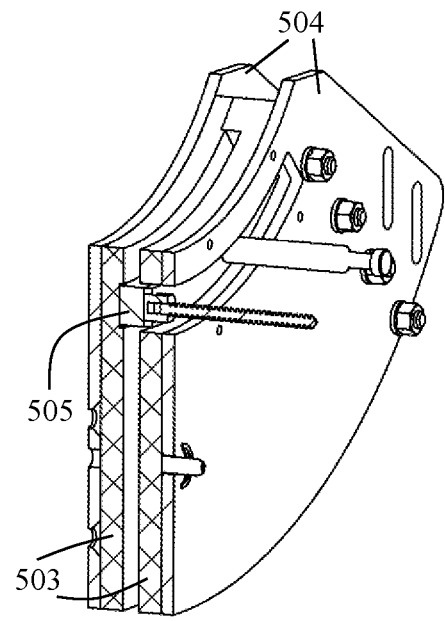
FIG. 5C is a sectional view of the fan beam collimator shown in FIG. 5A, illustratively showing a shutter in a closed position.

FIGS. 5A-5C illustrate at least one embodiment of a fan beam collimator that may be incorporated with the presently disclosed system. An x-ray beam 502 is emitted from an x-ray focal spot 501 and then enters into fan beam collimator 500 comprising two substantially parallel x-ray attenuating plates 503. For structural support, the collimator may further comprise two additional plates 504. Fan beam collimator 500 further comprises a shutter 505 which is moved to open and closed positions as in FIG. 5A and FIG. 5B, respectively. A linear motion drive, including without limitation a linear motor with lead screw 507, may be configured and disposed to move shutter 505 to the open and closed positions. Fan beam collimator 500 may also comprise guiding pins 506 configured and disposed to guide the motion of shutter 505.

To form an x-ray scanning pencil beam, an x-ray beam may be first collimated with a fan beam collimator. An embodiment of a fan beam collimator is illustrated in FIG. 5, where an x-ray beam 502 is emitted from an x-ray focal spot 501 and then enters the fan beam collimator comprising two substantially parallel plates 503 which are made from an x-ray attenuating material, including without limitation lead, tungsten or steel. Each of the plates 503 have a minimum thickness of 2 mm of lead or equivalent thickness of other material to achieve same attenuation as 2 mm of lead. To add structural support, the x-ray attenuating plates 503 may optionally be supported by two additional substantially parallel plates 504 made of material including without limitation steel or aluminum. The inner-outer position of the x-ray attenuating plates 503 and support plates 504 is switchable. Hence, in some embodiments of the present disclosure provide that x-ray attenuating plates 503 to be placed within support plates 504 as illustrated in FIG. 5, while in other embodiments the support plates 504 are placed within x-ray attenuating plates.

Fan beam collimator 500 comprises an x-ray shutter 505 which is moved into an open or closed position, as illustrated in FIG. 5B and FIG. 5C, respectively. When in the open position, the shutter 505 allows the x-ray beam to pass through the fan beam collimator, and when in the closed position, the shutter blocks x-rays from exiting the fan-beam collimator. The shutter 505 is made of x-ray attenuating material including without limitation lead or tungsten with a minimum thickness of 2 mm of lead or equivalent material thickness to achieve similar x-ray attenuation of 2 mm of lead or more. In the preferred fan beam collimator embodiment, the shutter 505 is moved to open or closed positions by means of linear motion drive such as motor with a lead screw 507, a linear actuator such as a solenoid, or other linear drivers known to a person skilled in the field. In other embodiments, a magnetic system is used to push and pull the shutter to open or closed positions. The magnetic system comprises one or more magnets to move the shutter when the one or more magnets are energized. The shutter may optionally comprise one or more guiding pins 506 to guide the motion of the shutter when moving between the open and closed positions.

Figure 6A:
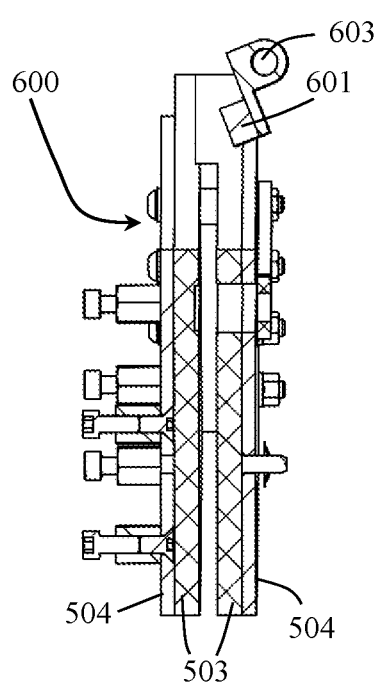
FIGS. 6A and 6B are cross-sectional views of a collimator having an embodiment of an x-ray shutter in an open and closed position, respectively, that may be incorporated with the presently disclosed system.
Figure 6B:
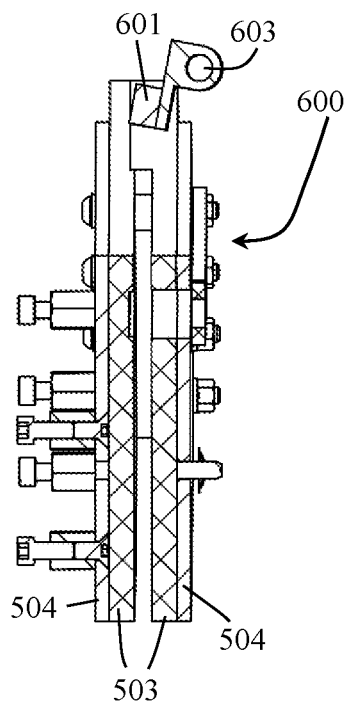

In one embodiment, the shutter 505 moves linearly into the open and closed positions as illustrated in FIGS. 5B and 5C. FIGS. 6A and 6B are sectional views of a collimator 600 having an embodiment of an x-ray shutter in an open and closed position that may be incorporated with the presently disclosed system.

In the alternative embodiment, as shown in FIGS. 6A and 6B, collimator 600 has shutter 601 configured and disposed to rotate around a hinge 603 to the open and closed positions, as illustrated in FIG. 6A and FIG. 6B, respectively.

In at least one embodiment, the x-ray beam shutter 505 is positioned within the fan beam collimator as illustrated in FIGS. 5A-5C. In some embodiments, the shutter may be positioned at the entrance of the fan beam collimator between the source of x-rays 501 and the fan beam collimator. Yet in other embodiments the shutter may be positioned at the exit of the fan beam collimator. The shutter position may be independent of the shutter motion, linear or rotating around a hinge.

In at least one embodiment, the shutter is formed into an arc shape as illustrated in FIGS. 5A-5C. In other embodiments, the shutter may be formed into a substantially straight shape. The shape of the shutter may be independent of its position. Hence, an arc shaped, or substantially straight shutter may be placed at the entrance, exit, or within the fan beam collimator. Similarly, the shutter shape may be independent of the shutter motion, linear or rotating around a hinge.

Figure 7A:
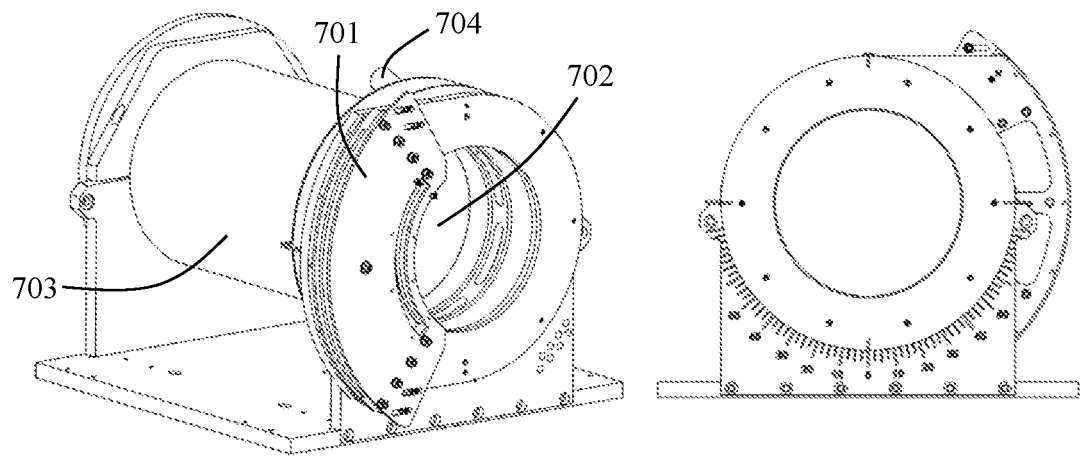
FIGS. 7A and 7B illustratively show a rotatable fan beam collimator that may be incorporated with the presently disclosed system.
Figure 7B:
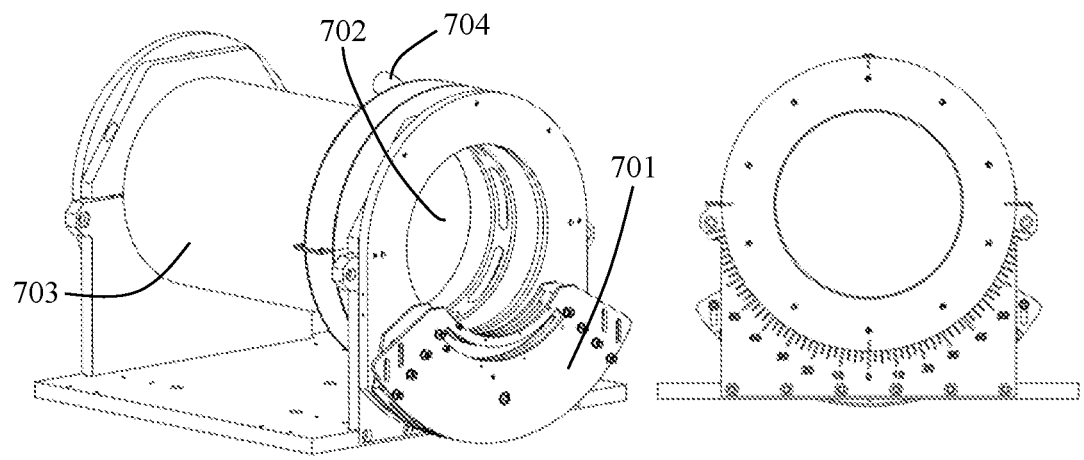

FIGS. 7A and 7B illustratively show a rotatable fan beam collimator 701 that may be incorporated with the presently disclosed system. FIGS. 7A and 7B illustrates sample rotation angles of fan beam collimator 701, which may be rotated around a bore 702. Bore 702, in enclosure 703, is configured and disposed to receive an x-ray tube, such as a unipolor x-ray tube, and have its body extending therethrough and its window in a line of sight with fan beam collimator 701. Fan beam collimator 701 may be rotated to the side, as shown in FIG. 7A, and may be rotated down as shown in FIG. 7B. In at least one embodiment, fan collimator 701 is configured and disposed to rotate 360 degrees about enclosure 703.

In some embodiments, as illustrated in FIGS. 7A and 7B, x-ray fan beam collimator 701 may be rotated around a bore 702 through which an x-ray tube extends such that the fan beam collimator 701 remains aligned with the x-ray beam window 202. In at least one embodiment of the presently disclosed system, the system is configured to rotate the x-ray tube with the rotation of fan beam collimator 701. Hence the x-ray tube and fan beam collimator 701 may be rotated to emit x-rays in any direction, including sideways, upwards, or downwards. The rotation of the fan beam collimator may be independent of the shutter. Hence, the fan beam collimator of the present disclosure, having or not having a shutter, may be rotated around bore 702, through which an x-ray tube extends, such that fan beam collimator 701 remains aligned with the x-ray beam window 202.

The fan beam collimator and shutter embodiments disclosed herein are not limited to a specific x-ray tube configuration. Hence, some embodiments of presently disclosed system comprise a rotatable fan beam collimator and shutter with a unipolar x-ray tube in a scanning pencil beam imaging system, while other embodiments comprise a rotatable fan beam collimator and shutter with a bipolar x-ray tube in a scanning pencil beam imaging system.

FIG. 8A illustratively shows an embodiment of an x-ray wheel 811 holding a sectioned x-ray attenuating ring that may be incorporated with the presently disclosed system. FIG. 8B illustratively shows the forming of a pencil beam with the sectioned x-ray attenuating ring. As illustrated in FIGS. 8A and 8B, x-ray wheel 811 having or holding a sectioned x-ray attenuating ring has one or more pencil beam bores 813 configured and disposed to rotate around a central axis or x-ray wheel 811 to create a scanning pencil beam which moves to cover an x-ray beam plane.

The presently disclosed system may have a sectioned x-ray attenuating ring held or incorporated with an x-ray wheel. For example, the x-ray attenuating ring may be divided into smaller segments which may enable a reduction in its width 805, thus reducing its overall weight or mass. The reduction in the mass of the attenuating ring reduces centrifugal forces placed on the x-ray wheel and the attenuating ring, which may relax constraints on the system parameters.

As illustrated in FIG. 8A, the width 805 of the sectioned x-ray attenuating ring may be reduced by providing the sectioned ring. Width 805 is less than a width of presently known non-sectioned x-ray attenuating rings. Therefore, the overall weight of the sectioned x-ray attenuating ring is less than that of the prior art x-ray attenuating ring. In at least one embodiment, as illustrated in FIG. 8A, the x-ray attenuating ring is divided into multiple segments 801 and 802. Segments 802 have pencil beam apertures 813. In this embodiment, the width of each segment 801 need not be wider than the pencil beam apertures 813, hence reducing the overall weight of the x-ray attenuating ring. Dividing the x-ray attenuating ring into segments also may have the benefit of simplifying its manufacturing process as smaller segments are generally easier to fabricate compared to a full ring.

FIG. 8B illustrates x-ray attenuating ring segments having apertures 803 having interlocking trapezoidal shapes. The trapezoidal shape may prevent, or substantially reduce, x-ray beams 822 emitted from an x-ray source 821 from passing between said ring segments. X-rays 824 exit the x-ray attenuating ring through apertures 803.

FIG. 8C illustratively shows another embodiment of a sectioned x-ray attenuating ring that may be incorporated with the presently disclosed system. The x-ray attenuating ring shown in FIG. 8C is divided into segments, hence its width 805 may be reduced as compared to currently used x-ray attenuating rings. The reduction in its width reduces its overall weight, which relaxes constraints on the system parameters. For example, the presently disclosed sectioned x-ray attenuating ring may comprise a plurality of segments, where a portion or all of the segments may have an aperture 813.

The embodiment of the sectioned x-ray attenuating ring shown in FIG. 8C is divided into four segments 803, each segment having a pencil beam bore or aperture 813. The number of segments may vary from a couple to a plurality, up to a hundred or more for example. The number of pencil beam bores in a segment may also vary from none to a plurality, up to a hundred or more for example. The number of pencil beam bores or apertures in a rotating x-ray wheel depends on the desired angular field of view. For example, in a system where the x-ray focal spot is centered at the geometrical center of the x-ray wheel, the embodiment illustrated in FIG. 8C comprising four pencil beam bores or apertures result in a 90° angular field of view. It is to be understood that the disclosed embodiments of the sectioned x-ray attenuating ring are no to be limited to the number of pencil beam apertures 813, the number or arc length of segments 801, 802, or 803, or the number of apertures 813 in the segments.

In the embodiment illustrated in FIG. 8A, the number of segments 801 need not be equal to the number of pencil beam apertures 813 and some embodiments of the disclosed system may have more segments 801 than segments 802, having pencil beam aperture 813. For example, each of the four segments 803 in the embodiment illustrated in FIG. 8C can be further divided into two pieces and the system may continue to function as intended. Similarly, in embodiments illustrated in FIG. 8C, some segments 803 may encompass no pencil beam bores 813 while other segments 803 may have more than one pencil beam bore 813. In other embodiments of the presently disclosed segmented or sectioned x-ray attenuating ring, some segments may comprise more than one pencil beam aperture 813 and other segment may have a different number of apertures 813 or be void of apertures 813. In each embodiment, the segments comprise an x-ray attenuating material including without limitation lead or tungsten.

The x-ray attenuating ring embodiments disclosed herein are not limited to a specific x-ray tube configuration. Hence, some embodiments of the disclosed system may comprise a combination of x-ray segments, segments having different arc lengths, segments having no or a plurality of pencil beam apertures 813, and x-ray segments 803. The presently disclosed x-ray attenuating ring may be configured to be disposed to rotate about a unipolar x-ray tube, bipolar x-ray tube, or other x-ray source in a scanning pencil beam imaging system.

In at least one embodiment, as illustrated in FIG. 8C, the x-ray attenuating ring is divided into multiple segments 803 encompassing x-ray pencil beam bores 813. Since each the segment is smaller and lighter than the full x-ray attenuating ring, it may be less susceptible to bend or break and hence each the segment may be made thinner, resulting in a lighter weight attenuating ring. Additionally, dividing the x-ray attenuating ring into segments may benefit or simplify its manufacturing process.

The segmented x-ray ring has each section made of an x-ray attenuating material such as lead or tungsten. The width 805 of the ring must be wider than that of the pencil beam bores 813 to avoid bending or breaking the x-ray ring proximate the x-ray pencil beam bores 813.

In at least one embodiment of the present disclosure, the mass of the attenuating ring does not exceed 22 pounds. In at least one other embodiment, the combined mass of both of the x-ray wheel and the x-ray attenuating does not exceed 60 pounds. In at least one additional embodiment, x-ray wheel comprises an x-ray attenuating material configured and disposed to substantially limit x-ray leakage from the x-ray system.

In at least one embodiment, the x-ray wheel comprises an air moving device configured and disposed to move air and to cool the x-ray system, upon the rotation of the x-ray wheel. For example, the x-ray wheel may have a configuration to draw or push air upon its rotation. The wheel may be rotated thousands of RPMs, around three thousand for example, and air may be moved simply under the Bernoulli effect. In at least one embodiment, the x-ray wheel has a non-uniform or a contoured surface for moving air. In at least one other embodiment, the x-ray wheel has fan blades extending toward the x-ray attenuating ring.

FIGS. 9A-9C illustratively show views of an enclosure cap 900 that may be incorporated with the presently disclosed system. X-ray enclosure cap 900 may be disposed to cover one or both ends of the x-ray tube enclosure and provide x-ray radiation shielding. X-ray enclosure cap 900 may be configured to allow air to pass therethrough, providing an air inlet or outlet in the enclosure. Enclosure cap 900 may comprise a material and thickness 903 sufficient to attenuate x-rays. As disclosed herein, x-ray attenuating materials may comprise lead, lead antimony, tungsten, and other materials known to a person skilled in the art. Enclosure cap 900 may comprise one or more openings 904 made at an angle. For example, the thickness of material 903 and the angle of openings 904 may be selected to provide x-ray shielding and air flow through. FIG. 9C shows openings 904 having a selected angle such that x-rays 902 emitted from a source of x-ray radiation 901 are substantially blocked when traveling in a straight path. Enclosure cap 900 may be configured to be attached to the x-ray shielding enclosure or to the x-ray tube.

In at least one embodiment, the presently disclosed x-ray system has at least one of the x-ray shields comprising an enclosure cap disposed with or proximate the first end or the second end of the enclosure. In at least one other embodiment, the enclosure cap comprises at least one of an air inlet and an air outlet.

Presently disclosed is a method of air cooling a scanning pencil beam x-ray system. The method comprise disposing an x-ray beam source proximate a first end of an enclosure; rotating an x-ray attenuating ring about the x-ray beam source; disposing at least one aperture in an outer circumference of the x-ray attenuating ring to x-rays generated with the x-ray beam source and forming a scanning pencil beam of x-rays; moving air into an air inlet in the enclosure; moving the air about the x-ray beam source and absorbing heat generated with the x-ray beam source; and moving the heated air out of the enclosure and thereby air cooling the scanning pencil beam x-ray system.

The method may comprise shielding at least one of the first end and a second end of the enclosure with an x-ray attenuating material, for example, disposing an enclosure cap proximate the shielded end of the enclosure. The method may further comprise moving air through the enclosure cap. Shielding of the first end of the enclosure may be performed with an x-ray wheel having or disposing the x-ray attenuating ring. The moving of the air in the scanning pencil beam x-ray system may be performed with the x-ray attenuating ring or an x-ray wheel having or disposing the x-ray attenuating ring.

An air moving device may be disposed of a perimeter of the x-ray attenuating ring, or an x-ray wheel having or disposing the x-ray attenuating ring, and the enclosure. The method may comprise directing air flow through at least one of an air inlet and an air outlet in the enclosure by disposing a plenum or chamber about an outer surface of the enclosure. The disposing of at least one aperture in an outer circumference of the x-ray attenuating ring may comprise disposing an x-ray wheel, having or disposing the x-ray attenuating ring, an axial distance from an x-ray beam plane source of at most 6 inches. The disposing of at least one aperture in an outer circumference of the x-ray attenuating ring may comprise disposing at most 22 pounds or the disposing the x-ray attenuating ring may comprise disposing the x-ray attenuating ring with an x-ray wheel and the disposing the x-ray attenuating ring and the x-ray wheel may comprise disposing at most 60 pounds.

The present disclosure provides systems and methods for creating a scanning pencil beam of x-rays and for the air cooling of the system. The system includes a shielded enclosure which allows for efficient air cooling of an x-ray tube enclosed inside the shielded enclosure. A fan beam collimator with compact x-ray shutter mechanism may be a part of the system. The fan beam collimator may be rotatable in all directions, 360 degrees about the enclosure. To reduce the overall weight of an x-ray attenuating ring, the present disclosure provides for a sectioned or segmented x-ray attenuating ring which may simplify its manufacturing process.

Aspects of the presently disclosed x-ray scanning pencil beam forming system comprise a shielded enclosure configured for the air cooling of the system. The system may have an x-ray fan beam collimator and an x-ray wheel with an x-ray attenuating ring. The embodiments and aspects of the x-ray scanning pencil beam forming system disclosed in the present application are illustrative and non-limiting.

The invention claimed is:

1. An air cooled x-ray system configured to form a scanning pencil beam of x-rays comprising:
   an enclosure having a first end and an opposite second end;
   an x-ray beam source configured to generate x-rays, the x-ray beam source is disposed in the enclosure proximate to the first end of the enclosure;
   an x-ray wheel having or holding an x-ray attenuating ring proximate to the first end of the enclosure, the x-ray attenuating ring having at least one aperture in an outer circumference thereof;
   the x-ray wheel being configured to rotate the x-ray attenuating ring about the x-ray beam source, wherein a passage of x-rays through the at least one aperture forms the scanning pencil beam;
   at least one air inlet disposed in x-ray system;
   at least one air outlet disposed in x-ray system;
   at least one air moving device configured to move air through the air inlet and the air outlet and to air cool the x-ray system, the at least one air moving device is disposed outside of a perimeter of the x-ray wheel and the enclosure; and wherein the enclosure comprises an x-ray attenuating material and is configured and disposed to substantially limit x-ray leakage from the x-ray system.

2. The x-ray system of claim 1, further comprising:
at least one x-ray shield disposed proximate the first end or the second end of the enclosure, wherein the at least one x-ray shield comprises an x-ray attenuating material configured to substantially limit x-ray leakage from the x-ray system.

3. The x-ray system of claim 1, wherein the x-ray wheel comprises an x-ray attenuating material configured to substantially limit x-ray leakage from the x-ray system.

4. The x-ray system of claim 1, wherein the x-ray wheel comprises one of the at least one air moving device, wherein the one air moving device is configured to move the air into the at least one air inlet and out of the at least one air outlet and to cool the x-ray system, upon the rotation of the x-ray wheel.

5. The x-ray system of claim 1, wherein the enclosure has at least one of the at least one air inlet, the at least one air outlet, and a plenum or chamber disposed about an outer surface, the plenum or chamber is configured and disposed to direct air flow through the at least one air inlet and outlet in the enclosure for air cooling the x-ray system.

6. The x-ray system of claim 1, wherein the x-ray wheel has a depth not to exceed 6 inches.

7. The x-ray system of claim 1, wherein the x-ray attenuating ring has a mass not to exceed 22 pounds or the x-ray wheel and the x-ray attenuating ring have a mass not to exceed 60 pounds.

8. The x-ray system of claim 2, wherein at least one of the first end of the x-ray shield and the second end of the x-ray shield comprises an enclosure cap disposed with or proximate the first end or the second end of the enclosure.

9. The x-ray system of claim 8, wherein the enclosure cap comprises at least one of the at least one air inlet and at least one air outlet.

10. A method of air cooling a scanning pencil beam x-ray system comprising the steps of:
disposing an x-ray beam source proximate a first end of an enclosure;
rotating an x-ray attenuating ring about the x-ray beam source;
generating x-rays with the x-ray beam source;
disposing at least one aperture in an outer circumference of the x-ray attenuating ring to allow a passage of the x-rays generated from the x-ray beam source to form the scanning pencil beam of x-rays;
disposing an air moving device outside of a perimeter of the x-ray attenuating ring or an x-ray wheel having the x-ray attenuating ring and the enclosure;
moving air into an air inlet in the enclosure, with the air moving device;
moving the air about the x-ray beam to absorb heat generated from the x-ray beam source; and
moving the heated air out of the enclosure to cool the scanning pencil beam x-ray system.

11. The method of claim 10, further comprising the step of:
shielding at least one of the first end and a second end of the enclosure with an x-ray attenuating material.

12. The method of claim 10, further comprising the step of:
shielding the first end of the enclosure with an x-ray wheel that has the x-ray attenuating ring.

13. The method of claim 10, further comprising the step of:
moving the air in the scanning pencil beam x-ray system with the x-ray attenuating ring or an x-ray wheel that has the attenuating ring.

14. The method of claim 10, further comprising the step of:
directing air flow through at least one of an air inlet and an air outlet in the enclosure by disposing a plenum or chamber about an outer surface of the enclosure.

15. The method of claim 10, wherein the disposing at least one aperture in an outer circumference of the x-ray attenuating ring comprises disposing an x-ray wheel, having or disposing the x-ray attenuating ring, an axial distance from an x-ray beam plane source of at most 6 inches.

16. The method of claim 10, wherein the disposing at least one aperture in an outer circumference of the x-ray attenuating ring comprises disposing at most 22 pounds, or wherein the method further comprises the step of:
disposing the x-ray attenuating ring with an x-ray wheel, wherein the x-ray attenuating ring and the x-ray wheel are at most 60 pounds.

17. The method of claim 11, wherein the shielding comprises disposing an enclosure cap proximate the shielded end of the enclosure.

18. The method of claim 17, further comprising the step of:
moving air through the enclosure cap.

19. An air cooled x-ray system configured to form a scanning pencil beam of x-rays comprising:
an enclosure having a first end and an opposite second end;
an x-ray beam source configured to generate x-rays, the x-ray beam source is disposed in the enclosure proximate to the first end of the enclosure;
an x-ray wheel having or holding an x-ray attenuating ring proximate to the first end of the enclosure, the x-ray attenuating ring having at least one aperture in an outer circumference thereof;
the x-ray wheel being configured to rotate the x-ray attenuating ring about the x-ray beam source, wherein a passage of x-rays through the at least one aperture forms the scanning pencil beam;
at least one air inlet disposed in x-ray system;
at least one air outlet disposed in x-ray system;
at least one air moving device configured to move air through the air inlet and the air outlet and to air cool the x-ray system;
wherein the x-ray wheel comprises one of the at least one air moving device and is configured to move the air into the at least one air inlet and out of the at least one air outlet and to cool the x-ray system, upon the rotation of the x-ray wheel; and
wherein the enclosure comprises an x-ray attenuating material and is configured and disposed to substantially limit x-ray leakage from the x-ray system.

20. A method of air cooling a scanning pencil beam x-ray system comprising the steps of:
disposing an x-ray beam source proximate a first end of an enclosure;
rotating an x-ray attenuating ring about the x-ray beam source;
generating x-rays with the x-ray beam source;
disposing at least one aperture in an outer circumference of the x-ray attenuating ring to allow a passage of the x-rays generated from the x-ray beam source to form the scanning pencil beam of x-rays;
moving air into an air inlet in the enclosure;

moving the air about the x-ray beam source to absorb heat generated from the x-ray beam source; and moving the air in the scanning pencil beam x-ray system with the x-ray attenuating ring or an x-ray wheel that has the attenuating ring, upon the rotating the x-ray attenuating ring.

\* \* \* \* \*